US011367324B2

(12) United States Patent
Crawford et al.

(10) Patent No.: US 11,367,324 B2
(45) Date of Patent: Jun. 21, 2022

(54) LIQUID BOTTLE PROCESSING AND REFILLING

(71) Applicant: International Business Machines Corporation, Armonk, NY (US)

(72) Inventors: Catherine H. Crawford, Bedford, NH (US); John A. Gunnels, Somers, NY (US); Ramya Raghavendra, New York, NY (US); Aisha Walcott, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 76 days.

(21) Appl. No.: 16/935,970

(22) Filed: Jul. 22, 2020

(65) Prior Publication Data

US 2022/0028206 A1    Jan. 27, 2022

(51) Int. Cl.
| B65B 1/04 | (2006.01) |
| G07F 17/00 | (2006.01) |
| A61L 2/18 | (2006.01) |
| B67D 1/08 | (2006.01) |
| A61L 2/07 | (2006.01) |

(52) U.S. Cl.
CPC ............ *G07F 17/0042* (2013.01); *A61L 2/07* (2013.01); *A61L 2/18* (2013.01); *B67D 1/0878* (2013.01); *G07F 17/0035* (2013.01); *A61L 2202/23* (2013.01)

(58) Field of Classification Search
None
See application file for complete search history.

(56) References Cited

U.S. PATENT DOCUMENTS

| 7,571,586 | B1* | 8/2009 | Morales | B08B 9/28 |
| | | | | 53/167 |
| 9,540,124 | B2 | 1/2017 | Petrini | |
| 9,731,845 | B2* | 8/2017 | Petrini | B08B 3/00 |
| 10,000,304 | B2 | 6/2018 | Moncayo, Jr. | |
| 10,846,975 | B2* | 11/2020 | Tansey, Jr | G07F 13/04 |
| 2013/0240079 | A1* | 9/2013 | Petrini | B08B 9/0821 |
| | | | | 141/1 |
| 2013/0240084 | A1 | 9/2013 | Carter et al. | |

(Continued)

FOREIGN PATENT DOCUMENTS

| AU | 2009234023 A1 | 10/2009 |
| AU | 2009234023 B2 | 6/2014 |

(Continued)

OTHER PUBLICATIONS

PCT, Notification of Transmittal of The International Search Report and The Written Opinion of The International Searching Authority, or The Declaration for Application PCT/CN2021/107324 dated Oct. 20, 2021.

*Primary Examiner* — Sunit Pandya
(74) *Attorney, Agent, or Firm* — Patterson + Sheridan, LLP

(57) ABSTRACT

Techniques for providing a reusable filled bottle are provided. A stations receives a bottle request from a user and uses information from the request to select and associate a sanitized bottle to the user. The user is charged for a bottle rental and provided with a filled reusable bottle. The user may also return the bottle to the station to have the bottle refilled or return the bottle such that the bottle rental is completed and the bottle no longer associated with the user.

20 Claims, 9 Drawing Sheets

(56) References Cited

U.S. PATENT DOCUMENTS

2015/0329225 A1\* 11/2015 Moncayo, Jr. ............ A61L 2/07
53/426
2017/0088296 A1 3/2017 Petrini

FOREIGN PATENT DOCUMENTS

| | | |
|---|---|---|
| BR | PI0906308 A2 | 7/2015 |
| CA | 2720624 A1 | 10/2009 |
| CA | 2813021 A1 | 4/2012 |
| CN | 102015515 A | 4/2011 |
| CN | 102015515 B | 8/2013 |
| CN | 206659686 U | 11/2017 |
| CN | 206910225 U | 1/2018 |
| CN | 107679957 A | 2/2018 |
| CN | 107886639 A | 4/2018 |
| EP | 2271580 A1 | 1/2011 |
| EP | 2271580 A4 | 12/2011 |
| EP | 2625134 A4 | 9/2016 |
| JP | 2011521312 A | 7/2011 |
| MX | 2010010685 A | 4/2011 |
| WO | 2009126481 A1 | 10/2009 |
| WO | 2018194211 A1 | 10/2018 |
| WO | 2018224864 A1 | 12/2018 |
| WO | 2019071983 A1 | 4/2019 |

\* cited by examiner

LIQUID BOTTLE PROCESSING AND REFILLING

BACKGROUND

The present disclosure relates to providing a liquid filled reusable bottle to a user through a bottle station and providing a bottle sharing program for reusable bottles.

People often need access to water/hydration in public places such as in transit centers (bus stations, train stations, airports, etc.), fitness centers, education institutions, retail environments, and workplaces among other public places. Many public places offer access to water and other beverages, but these methods can often produce unnecessary waste through the production of disposable cups or disposable bottles. Additionally, some water access sources may be a source of unsanitary conditions such as a water fountain or water cooler, where a user may not be sure whether the water is safe for drinking. Access to sanitary and reliable water where the water may also be transported in containers away from the water source, without creating additional waste, remains difficult.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method. The method also includes receiving a bottle request from a user, selecting a sanitized bottle from a bottle storage, associating the selected sanitized bottle to a user account for the user, charging the user account for a bottle rental, and filling the associated bottle with liquid, and providing the filled bottle to the user. Advantageously, the method provides for a bottle reuse method and system that provides users with reusable bottles and hydration without producing extra waste in the form of disposable bottles. Other embodiments of this aspect include corresponding computer systems, apparatus, and computer programs recorded on one or more computer storage devices, each configured to perform the actions of the methods.

According to another embodiment of the present disclosure, the method may include: receiving a bottle intake request from the user, accepting a used bottle from the user in response to the bottle intake request, performing an intake process for the used bottle, and updating the user account for the user with an indication of a returned bottle. Advantageously, this allows a user to return a bottle to a station for reuse reducing waste production as well as allowing a user to keep possession of the water bottle.

According to still another embodiment of the present disclosure, performing the intake process may include: performing a structural review of the used bottle, sanitizing the used bottle, completing a charge for the bottle rental, and storing the sanitized used bottle in a bottle storage structure. Advantageously, this allows for a bottle to be reused by a station without needing external interactions, such as a restocking of the machine.

According to still another embodiment of the present disclosure, performing the intake process may include: performing a structural review of the used bottle; completing a charge for the bottle rental; and storing the used bottle in a used bottle storage for external sanitation. Advantageously, this allows for some bottles to be removed from the system for further inspection, sanitation, or for disposal as needed.

According to another embodiment of the present disclosure, the user account is associated with a bottle subscription service where associating the selected bottle to the user account may include: verifying the user is a member of the bottle subscription service. In an example where when the user is not a member of the bottle subscription service, the method may include intaking the user as a new member of the bottle subscription service and when the user is a member of the bottle subscription service the method may include: verifying a payment method or paid subscription for the user, and updating a bottle count associated with the user with the selected bottle. These embodiments allow for a user to repeatedly access reusable bottles via a user account.

According to another embodiment of the present disclosure, filling the associated bottle with liquid may include: receiving an enhancement selection from the user and providing an additive with the liquid while filling the selected bottle. An advantage of such an embodiment is that a user may access both liquids such as water along with additional types of flavors via a single bottle egress.

According to another embodiment of the present disclosure, the user account is associated with a health profile for the user, where the method further may include: determining an amount of liquid in the filled bottle and updating a liquid tracking count for the user in the health profile for the user. An advantage of such an embodiment is that a user is able to track hydration levels and liquid intake.

According to still another embodiment of the present disclosure, the method may also include: receiving a refill request from the user, accepting a refill bottle from the user in response to the refill request, sanitizing the refill bottle, filling the refill bottle with liquid, and providing the filled refill bottle to the user. Advantageously, this allows for a bottle associated with a user to be sanitized and filled for the user without needing external interactions, such as needing a new bottle. Implementations of the described techniques may include hardware, a method or process, or computer software on a computer-accessible medium.

In another example embodiment, a system for bottle rental and sharing is provided. The system includes a bottle storage structure including at least one bottle. The system also includes a bottle sanitizer. The system also includes a user interaction system which may include a user interface and a bottle egress. The system also includes a liquid dispenser and a control system may include one or more computer processors and a memory containing a program which when executed by the computer processors performs an operation. The operation may include: receiving a bottle request from a user via the user interaction system, selecting a sanitized bottle from the bottle storage structure, associating the selected sanitized bottle to a user account for the user, charging the user account for a bottle rental, filling the associated bottle with liquid via the liquid dispenser, and providing the filled bottle to the user via the bottle egress. Other embodiments of this aspect include corresponding computer systems, apparatus, and computer programs recorded on one or more computer storage devices, each configured to perform the actions of the methods.

DETAILED DESCRIPTION

People often need access to drinkable water in various circumstances while away from home or without access to a reusable water container (e.g., a water cup or bottle). While the embodiment herein specifically describe drinkable water, the techniques, systems, and apparatuses discussed below can apply to any type of drinkable liquid such as soda, juice, seltzer, and the like. Many solutions exist to provide drinkable water to people. For example, water fountains are often found in public places and provide quick and easy access to water. In many cases, these water fountains offer chilled and filtered water which can be provided directly to a person using the water fountain or can be used to fill a water container such as a bottle, etc. However, the sanitation level of water fountains cannot be guaranteed and must be repeatedly visited by those without a water container in order to gain access to water.

In many cases, someone in a public place without a fillable container, would need to make multiple trips to the water fountain in order to stay hydrated. For example, someone exercising in a gym or working at a work station must make several trips to a water fountain or other water source to stay hydrated when he or she does not have a water container.

Additionally, as described above, people often need access to water in public places such as in transit centers (bus stations, train stations, airports, etc.), fitness centers, education institutions, retail environments, and workplaces among other public places when they have forgotten or do not otherwise have access to a reusable water container. The systems and methods described herein provide for a low waste reusable bottle sharing system and program where a user may access a sanitized reusable bottle which is filled with water without concern of contamination at the water source.

Figure 1A:
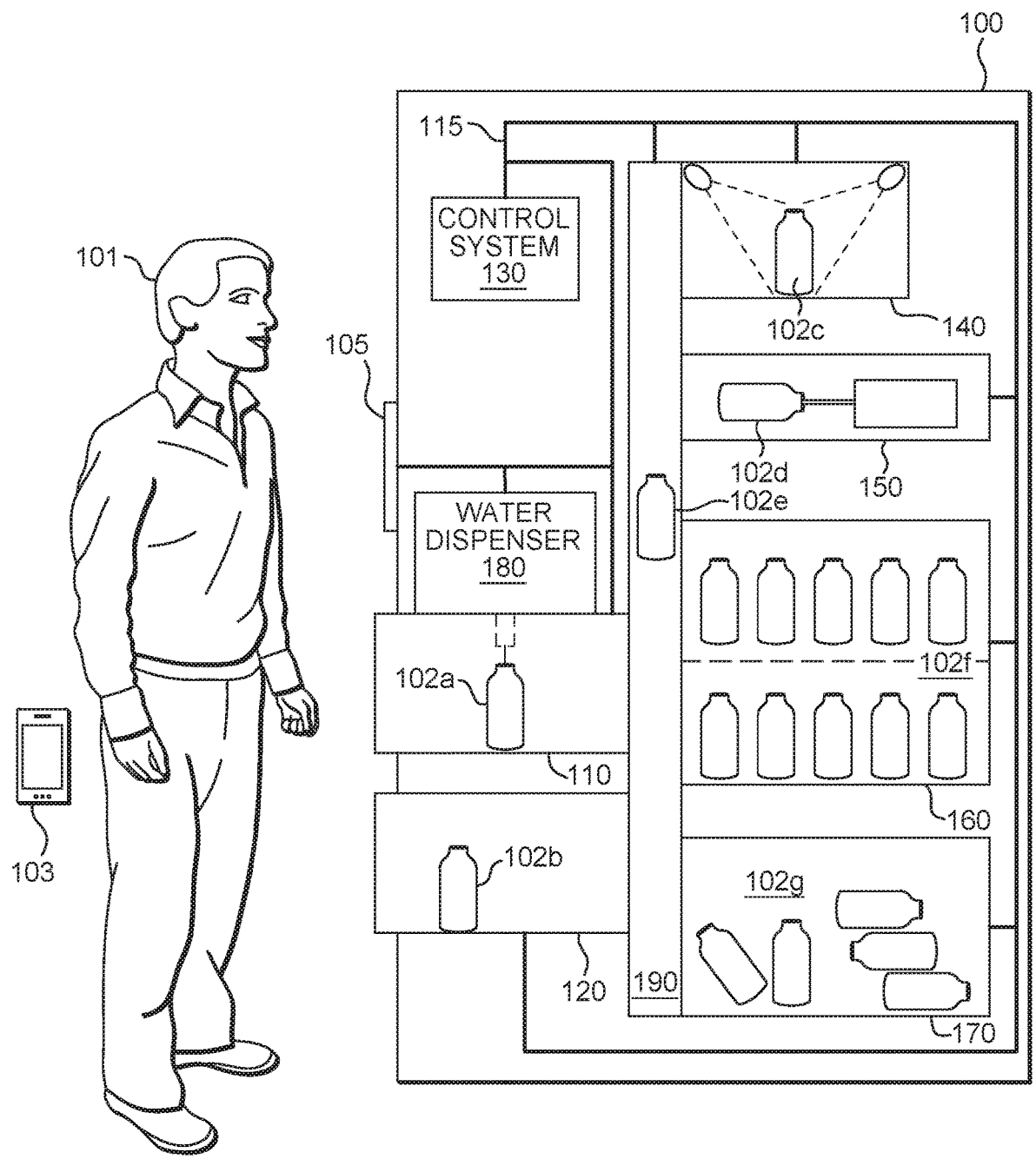
FIG. 1A illustrates a side view cross-section of a bottle processing station, according to embodiments described herein.
Figure 1B:
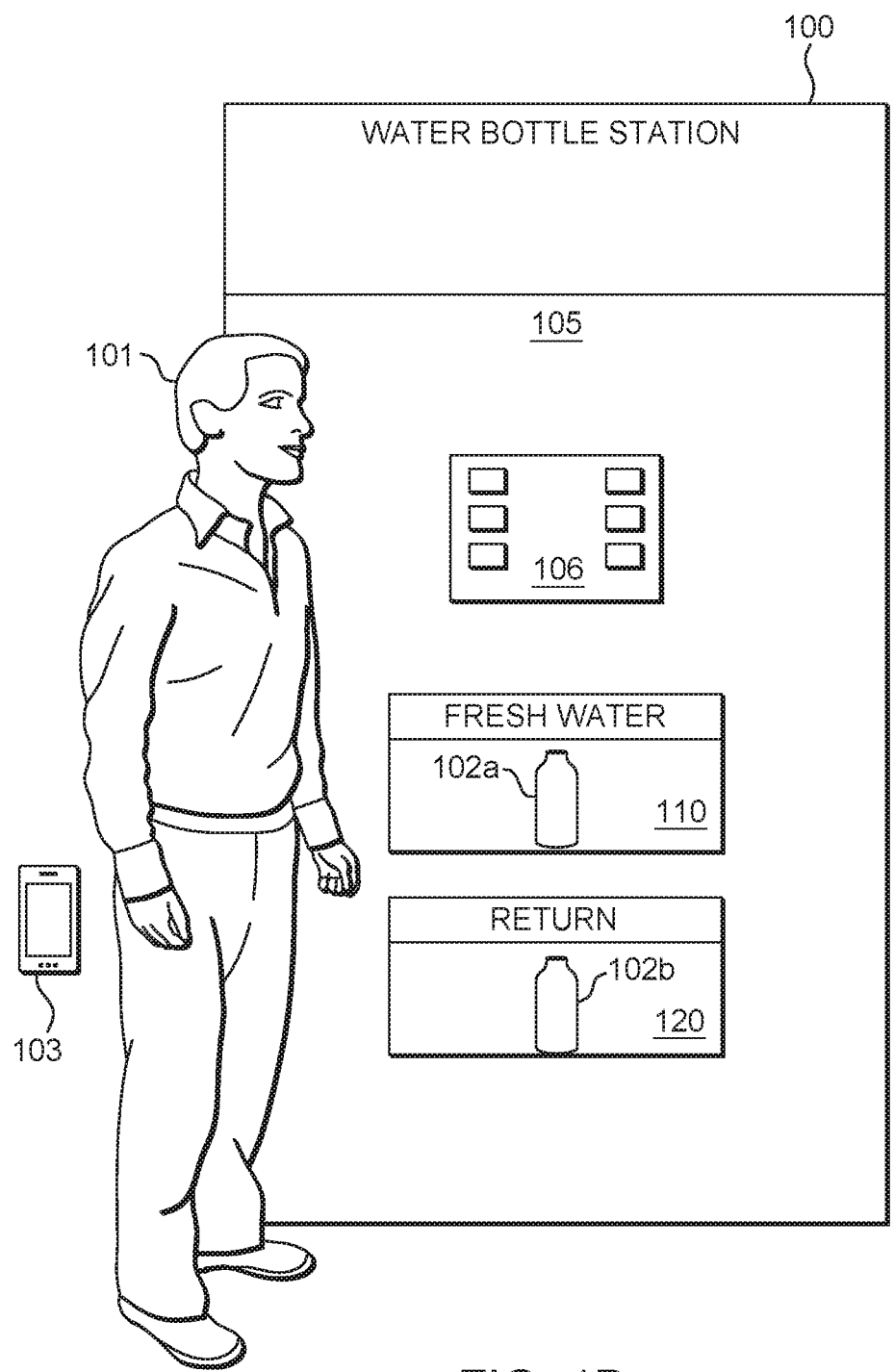
FIG. 1B illustrates a front view of a bottle processing station, according to embodiments described herein.

FIG. 1A illustrates a side view cross-section of a bottle processing station, station 100 and FIG. 1B, illustrates a front view of the station 100, according to embodiments described herein. The station 100 includes various systems and modules that provide for a user 101 to interact with the station 100 to receive a filled bottle 102a and to return a bottle 102b. In some examples, the user 101 interacts with the station 100 via a user interface 105. For example, the user 101 may interact with components on a screen 106 as shown in FIG. 1B to select various options for interacting with the station 100. The user interface 105 is described in more detail in relation to FIG. 2. In some examples, the user 101 may interact with a mobile device 103 (e.g., a user device such as a smart phone or other device) in communication with the station 100 in order to receive or return a bottle.

In some examples, the user 101 requests a bottle from the station 100 via the user interface 105. The user interface 105 communicates to the control system 130 via a communication bus 115, the control system 130 determines various actions to be performed by the components of the station 100 in order to provide a filled bottle to the user 101. The station 100 includes a bottle handler 190 which includes components to transfer the various bottles described herein between the plurality of components/subsystems of the station 100. For example, the bottle handler 190 is transferring the bottle 102e between the components of the station 100.

In one example, in response to a bottle request from the user 101, the control system 130 instructs a bottle handler 190 to retrieve a bottle from a bottle storage 160 which includes a plurality of sanitized bottles, the bottles 102f, within a storage structure. The bottle handler 190 selects a bottle from the bottle storage 160 and transfers the bottle to a bottle egress 110. In some examples, the bottle egress 110 is associated with a liquid dispenser 180 as described in more detail in relation to FIG. 5. The liquid dispenser 180 includes a liquid source and filling system to fill a bottle 102a with water or other liquid and any additional water or other type additives. When the bottle 102a is filled, the bottle egress 110 provides the filled bottle 102a to the user 101. For example, the user 101 may retrieve the bottle 102a from the egress 110 as shown in FIG. 1B.

When the user 101 has consumed water or other liquid from a bottle or otherwise wishes to return a bottle to the station 100, the user 101 may interact with the user interface 105 to request a bottle return or request a bottle refill. In some examples, the user 101 returns the bottle 102b to a bottle ingress 120 as shown in FIG. 1B and the bottle handler 190 transfers the bottle 102b to a bottle inspection system 140. The bottle inspection system 140 includes sensors and other components to physically examine a bottle, such as the bottle 102c, to assess a compatibility of the bottle 102c with the station 100 and assess the physical condition of the bottle 102c to verify the bottle is in good condition. The bottle inspection system is described in more detail in relation to FIG. 3.

In some examples, the bottle handler 190 also transfers the bottle 102b to a bottle sanitizer 150. In some examples, the bottle sanitizer 150 washes bottles for storage or reuse. For example, the bottle sanitizer 150 applies a washing flow to a bottle 102d to remove any debris or other contents from the bottle 102d and also provides a sanitizing flow such as steam or a sanitizing solution to the bottle 102d. The bottle sanitizer 150 may also dry the bottle 102d and prepare the bottle 102d for storage or water/liquid refill. For example, once the bottle 102d is sanitized and dried, the bottle handler 190 may transfer the bottle 102d to the bottle storage 160 for storage. In another example, once the bottle 102d is sanitized and dried the bottle handler 190 may return the bottle 102d to the bottle egress 110 to fill the bottle with water via the liquid dispenser 180.

In another example, bottles may be stored in a bottle storage 170. In some examples, the bottle storage 170 stores returned bottles that are damaged or require external servicing. For example, bottles 102g may include damaged bottles, overflow bottles when the bottle storage 160 is full, incompatible bottles, or bottles stored for external sanitization.

In some examples, as the station 100 processes bottles through the various components of the station 100, the user interface 105 updates the display 106 (and or a display on the mobile device 103) in order to provide the user 101 with an indication of the bottle status. For example, the display 106 may display a wait time for a filled bottle, an indication of a completed return, etc. The various subsystems of the station 100 are described in more detail in relation to FIGS. 2-5.

Figure 2:
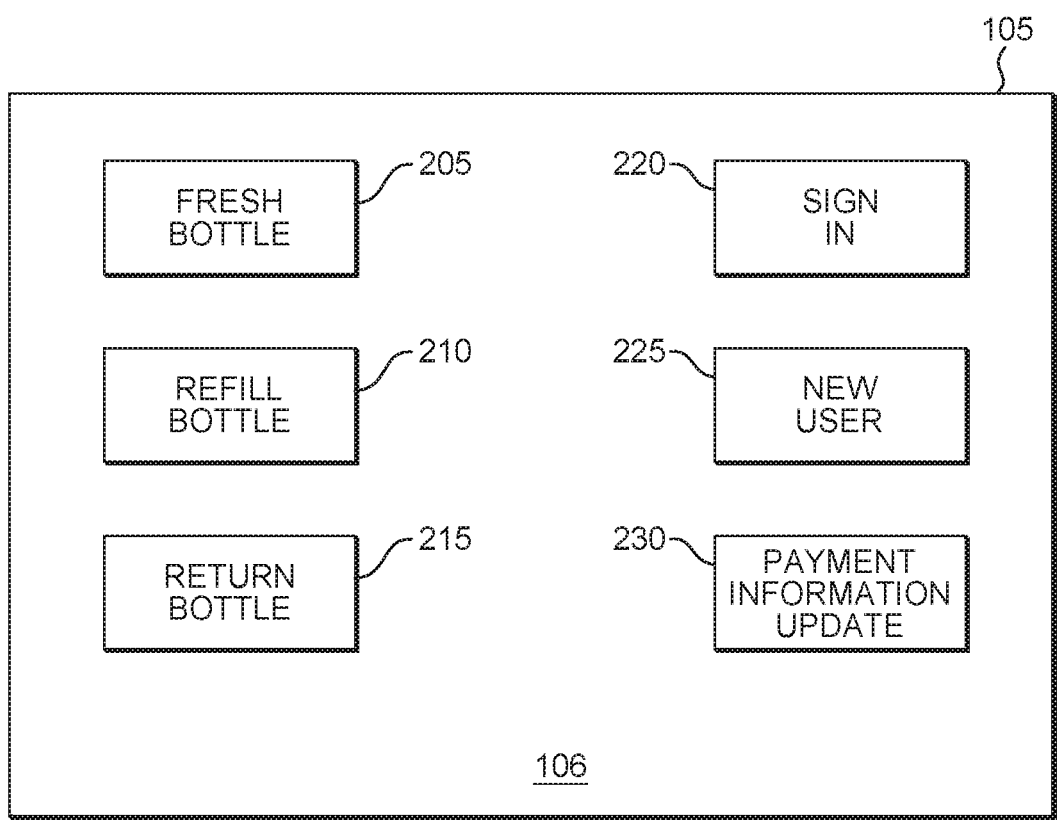
FIG. 2 illustrates a user interface, according to embodiments described herein.

FIG. 2 illustrates the user interface 105, according to embodiments described herein. The user interface includes the display 106 and user interface elements 205-230. While shown on the display 106 which is integrated into the station 100, the user interface 105 and the user interface elements 205-230 may also be provided via a user interface on the mobile device 103. For example, an application associated with the station 100 may be installed on the mobile device 103 such that the user may interface and communicate with the station 100 via the mobile device 103.

Example user interface elements may include user interface elements to request specific actions from the station 100. For example, the UIE 205 may initiate a bottle request process from the station 100. The UIE 210 initiates a bottle refill process and the UIE 215 initiates a bottle return process. The UIEs 220, 225, and 230 initiate processes related to a user profile for the station 100. For example, sign in, sign up, and payment information processes may be initiated with the selection of the UIEs 220, 225, 230. The user profile information may be used at other connected stations related to the station 100 in order to provide users access to reusable bottles in multiple locations.

Figure 3:
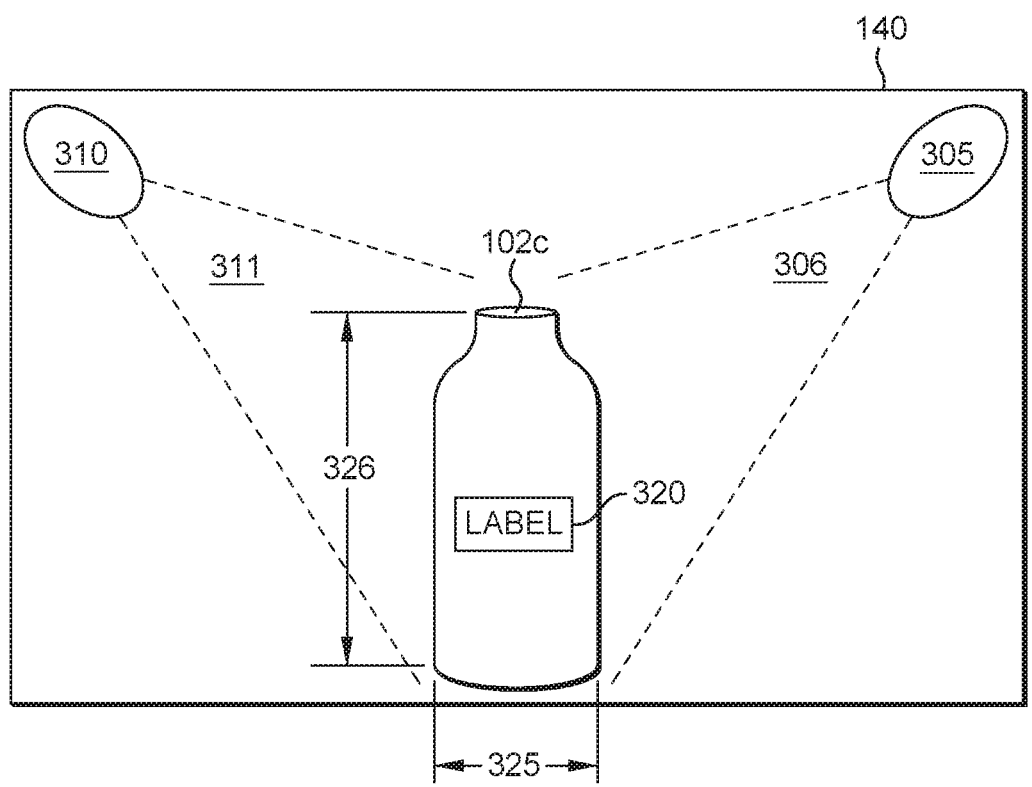
FIG. 3. illustrates a bottle inspection system, according to embodiments described herein.

FIG. 3. illustrates the bottle inspection system 140, according to embodiments described herein. As described in relation to FIG. 1A, the bottle inspection system 140 examines and verifies that a bottle is compatible with the station 100 and is undamaged.

In some examples, the bottle 102c includes physical dimensions 326 and 325 and/or a label 320 which are used by the bottle inspection system 140 to determine the compatibility of the bottle 102c with the station 100. For example, a bottle is compatible with the system when the physical dimensions 326 and 325 are within given parameters indicating the bottle can physically fit in each of the subsystems in the station 100. For example, a bottle which is too large or too small for the station 100 may be rejected by the bottle inspection system 140 and returned to a user.

In some examples, the bottle inspection system 140 includes visual sensors 305 and 310 which perform visual inspections 306 and 311 of the bottle 102c which can determine the physical dimensions 326 and 325 of the bottle 102c as well as identified label 320 or other physical attributes of the bottle 102c (e.g., a material of the bottle). In some examples, the bottle inspection system 140 allows for a bottle to be associated with the station 100 without needing electronic components (e.g., RFID tags) installed on the bottle 102c. For example, electronic components installed on the bottle 102c may be damaged during the sanitation and water/liquid filling process in the station 100. Station 100 avoids these problems by utilizing the bottle inspection system 140 to process the bottles in the station 100.

The visual inspections 306 and 311 may also identify damage such as dents or cracks in the bottle 102c. When the visual inspections 306 and 311 indicate damage to the bottle, the station 100 may return the bottle to the user, charge the user for damage to the bottle, and/or move the damaged bottle to bottle storage 170 for removal from the station 100. In some examples, the bottle 102c upon visual inspection and verification in the bottle inspection system 140 is sanitized for further use or storage in the station 100.

Figure 4:
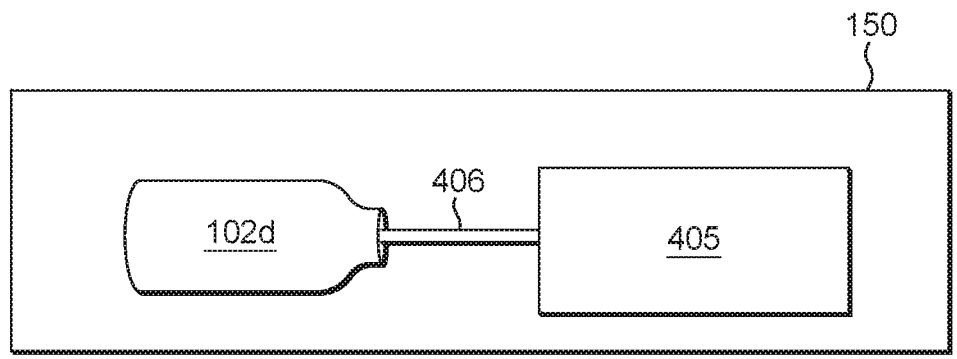
FIG. 4 illustrates a bottle sanitizer, according to embodiments described herein.

FIG. 4 illustrates a bottle sanitizer, according to embodiments described herein. The bottle sanitizer 150 includes bottle washer 405 which provides a cleaning flow 406 to bottle 102d. The cleaning flow 406 may include water, steam, and/or a cleaning solution that removes any debris from the bottle 102d. In some examples, the cleaning flow 406 also sanitizes the bottle 102d such that the bottle 102d may be stored for future use or refilled and provided back to a user. In an example where the bottle is to be stored, the bottle handler 190 transfers the sanitized bottle from the bottle sanitizer 150 to the bottle storage 160. In an example where the bottle is to be refilled with water, the bottle handler 190 transfers the bottle to the bottle egress 110 to be refilled with water from the liquid dispenser 180.

Figure 5:
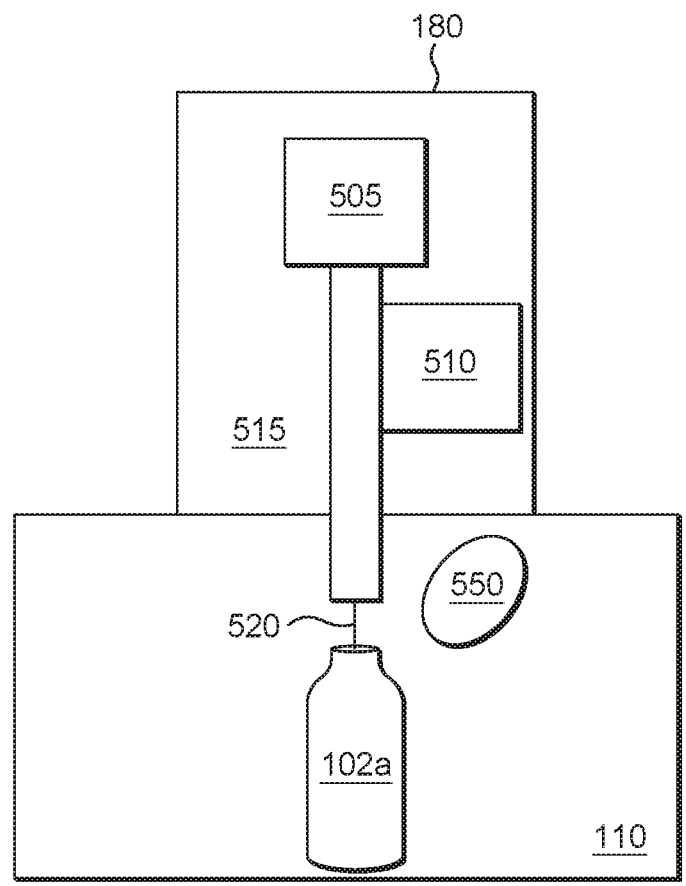
FIG. 5. illustrates a liquid dispenser and a bottle egress system, according to embodiments described herein.

FIG. 5 illustrates the liquid dispenser 180 and the bottle egress 110, according to embodiments described herein. While shown together, the liquid dispenser 180 may be located in a different location within the station 100. For example, the liquid dispenser 180 may fill the bottle 102a prior to the bottle 102a being transferred to the bottle egress 110. The liquid dispenser 180 includes a liquid source 505 and nozzle 515 which provides the liquid flow 520 to fill the bottle 102a. In some examples, the liquid dispenser 180 includes additive system 510 which may add a liquid additive (e.g., water flavoring, sports enhancements, nutritional enhancements such as those commonly used to support rigorous physical activity, etc.) to the liquid flow 520 according to user selections. For example, the liquid dispenser 180 may provide a flavored liquid to the bottle 102a. The liquid dispenser 180 also includes a sensor 550 which measures or otherwise determines an amount of liquid in provided to the bottle 102a. When a liquid level in the bottle 102a reaches a threshold as determined by the sensor 550, the liquid dispenser 180 may stop filling the bottle 102a to prevent liquid overflow. In one example, the sensor 550 determines an amount of liquid provided to the bottle 102a and updates a user profile with an amount of liquid provided to the user 101 via the bottle 102a. When the bottle 102a is filled, the station 100 provides the filled bottle to the user via the bottle egress 110 as described in more detail in relation to the method of FIG. 6.

Figure 6:
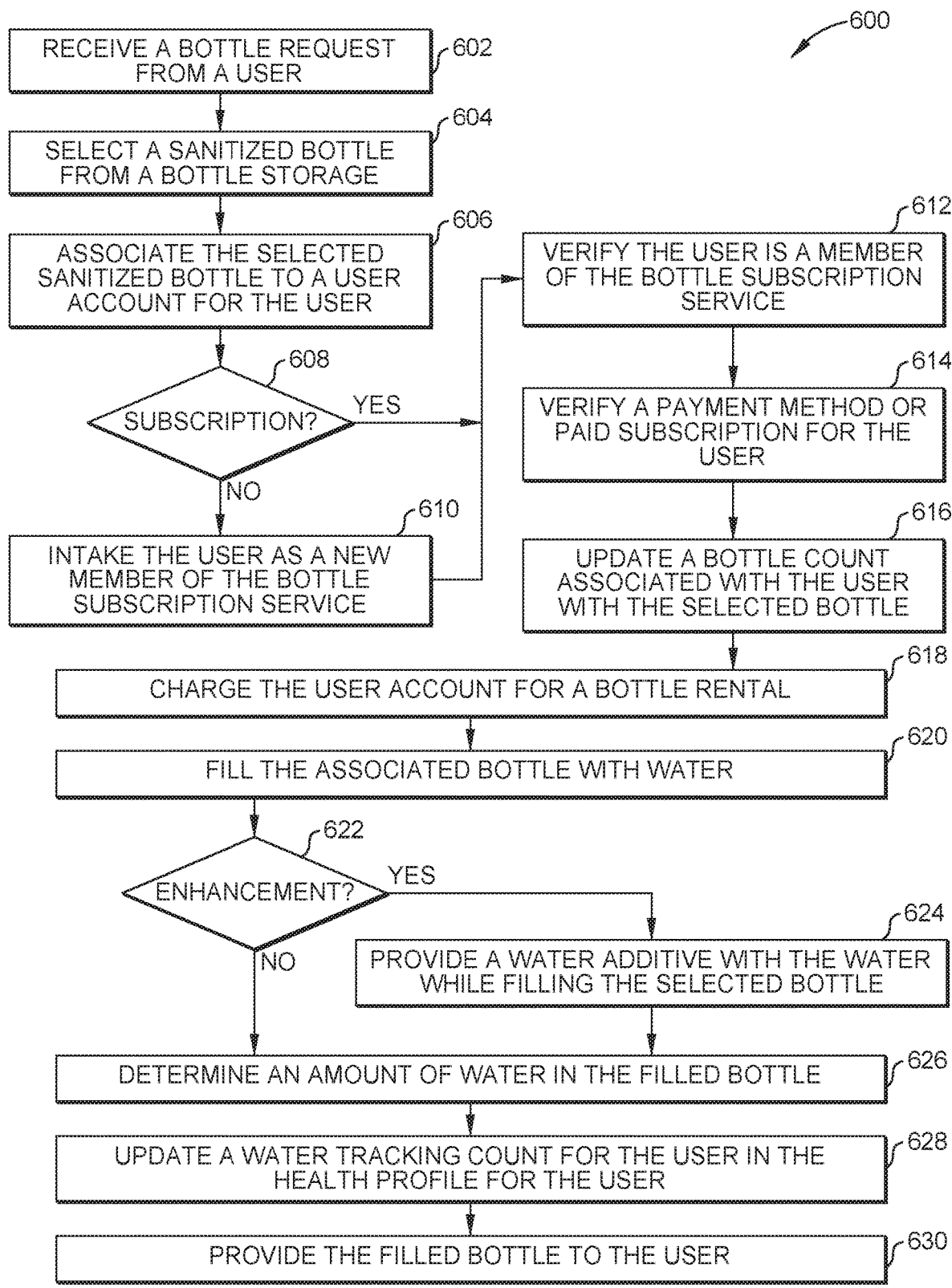
FIG. 6 is a method for providing a bottle to a user, according to embodiments described herein.

FIG. 6 is a method 600 for providing a bottle to a user, according to embodiments described herein. For ease of discussion the methods described in FIGS. 6-8 will refer to the examples and station 100 as described in FIGS. 1A-5 and the control system 130 described in relation to FIG. 8. Method 600 begins at block 602 where the station 100 receives a bottle request from a user. In many examples, the user 101 may be away from home without access to a bottle or liquid container. In order to reduce waste through the form of single use bottles such as disposable plastic bottles, the user 101 may desire to select a reusable bottle from the station 100. In some examples, the station 100 is located in public areas such as fitness centers, transit centers (e.g., train or bus stations), schools, retail centers, or other areas where the user may desire a bottle.

In some examples, the user 101 may already have an account with a bottle service associated with the station 100 or the user 101 may be a new user. In both examples, the user may interact with the user interface 105 to input a request for a new bottle. For example, the user may selected the UIE 205 to receive a fresh bottle on the display 106 described in FIG. 2. In another example, the UIE 205 may be provided on the mobile device 103 such that the user does not need to physically interact with the display 106 on the station 100. The station 100 begins the process to provide the user 101 with a filled bottle in response to the bottle request from the user 101.

At block 604, the station 100 selects a sanitized bottle from a bottle storage. For example, the station 100 via the bottle handler 190 and the sanitized bottle storage 160 selects a bottle from the sanitized bottles 102f In some examples, the sanitized bottles include bottles that have been sanitized via the bottle sanitizer 150 and stored in the bottle storage 160 as described in relation to blocks 710 and 712 of FIG. 7. In some examples, the bottle storage 160 includes bottles that are externally sanitized from the station 100 and stocked into the station 100 by a service agent.

At block 606, the station 100 associates the selected sanitized bottle to a user account for the user. For example, the station 100 may update a number of bottles currently assigned or rented by the user 101 as stored in a user profile 921 discussed in FIG. 9. In some examples, associating the selected sanitized bottle includes the method steps described in relation to blocks 608-616.

At block 608, the station 100 determines whether a user is associated with a subscription to the station 100. For example, the user 101 may be prompted to sign in to a user account via the user interface 105. In some examples, the user 101 may already have signed into the station 100 using the UIE 220 or may have initiated a new account via the UIE 225. In an example where the user 101 is not yet associated with the subscription service, the method 600 continues to block 610 where the station 100 intakes the user as a new member of the bottle subscription service. The intake process for the user may include acquiring contact information, payment information, and verifying an identification of the user 101 and storing the collected information in the user profile 921. When the intake process is complete at block 610 and when the user 101 is associated with the subscription to the station 100 at block 608, the method 600 proceeds to block 612.

At block 612, the station 100 verifies the user is a member of the bottle subscription service. For example, the station 100 verifies that the user profile 921 associated with the user 101 is current and includes contact information and identification information. In an example where the information is out of date, the station 100 may perform a process to update the user profile 921 prior to adding the bottle to the user account. For example, contact information, payment information, or other information related to the user 101 is updated in the user account information and the user profile 921 prior to proceeding to block 614.

At block 614, the station 100 verifies a payment method or paid subscription for the user. For example, the station 100 verifies that the payment method stored in the user profile 921 is valid and can be charged. For example, the station 100 may initiate a test charge to verify the payment will accept the charge. In another example, the user may also have a pre-paid or post-paid subscription where each bottle is not charged, but the user can access the station 100 as an ongoing service. In this example, the station 100 verifies that the subscription is valid.

At block 616, the station 100 updates a bottle count associated with the user with the selected bottle. For example, the user profile 921 includes a bottle count with a number of bottles currently associated with the user 101. For example, the user 101 may have multiple bottles rented or checked out from the station 100 (and other associated stations) at any given time. The station 100 updates the bottle number of the bottle count once the subscription information is verified.

At block 618, the station 100 charges the user account for a bottle rental. In some examples, charging the user account includes updating the subscription information associated with the user 101 (e.g., adding the bottle to a subscription). In another example, such as a pay-per-bottle model, the user account is charged an initial rental charge or temporary hold charge for the bottle rental.

At block 620, the station 100 fills the associated bottle with liquid. For example, as shown in FIG. 5, the station 100 provides a liquid flow 520 from the liquid source 505 to the bottle 102a. At block 622, the station 100 determines whether an enhancement selection has been received from a user or is stored in a user profile. For example, the station 100 may receive a liquid enhancement selection from the user via the user interface 105. When an additive is selected, the method 600 proceeds to block 624 where the station 100 provides a liquid additive with the liquid while filling the selected bottle. For example, the additive system 510 adds a liquid enhancement to the liquid flow 520 while the filling the bottle 102a.

At block 626, the station 100 determines an amount of liquid in the filled bottle and updates a liquid tracking count for the user in the health profile for the user at block 628. In some examples, the determined amount of liquid in the filled bottle is determined via the sensors 550. In some examples, the liquid dispenser 180 stops providing liquid when a defined amount of liquid is provided to the bottle 102a. For example, when a fill line or fill amount for the bottle 102a or an amount selected by the user 101 is reached, the liquid dispenser 180 stops the flow to the bottle 102a. In some examples, the determined amount is added to a health profile for the user that tracks an amount of liquid consumed by the user.

At block 630, the station 100 provides the filled bottle to the user. For example, the station 100 provides the bottle 102a to the user 101 via the bottle egress 110. In some examples, the user interface 105 is updated to indicate that the bottle 102a is ready for pick up by the user 101. The bottle 102a may then be utilized by the user 101 and the liquid consumer by the user 101. When the user 101 is finished using the bottle 102a, the user may then return the bottle to the station 100 to avoid producing excess waste as described in FIG. 7.

Figure 7:
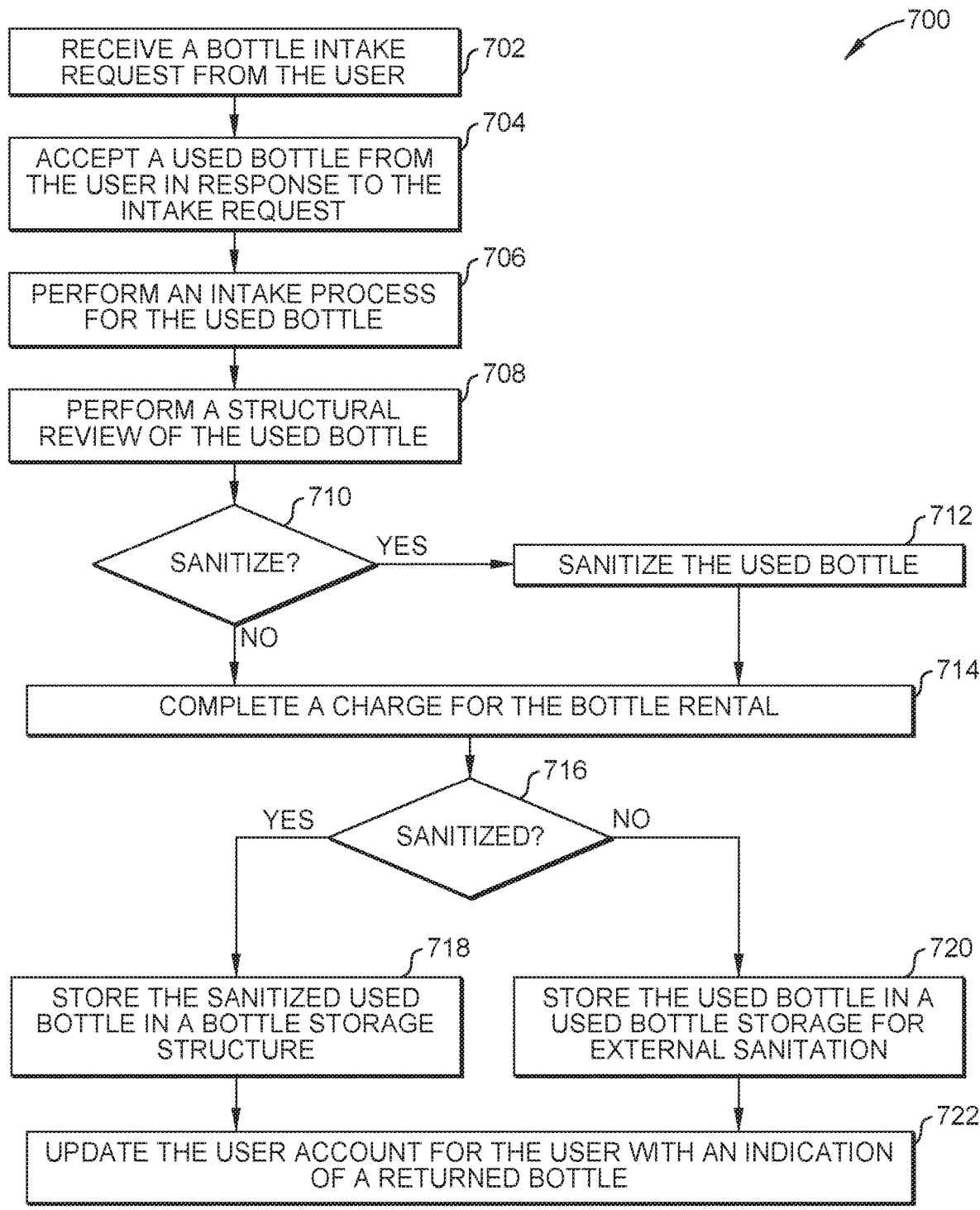
FIG. 7 is a method for receiving a bottle from a user, according to embodiments described herein.

FIG. 7 is a method 700 for receiving a bottle from a user, according to embodiments described herein. Method 700 begins at block 702 where the station 100 receives a bottle intake request from the user. For example, the user 101 may interact with the user interface 105 to input a request for to return a bottle. For example, the user may selected the UIE 215 to return a used bottle on the display 106 described in FIG. 2. In another example, the UIE 215 may be provided on the mobile device 103 such that the user does not need to physically interact with the display 106 on the station 100. The station 100 begins the process to intake the bottle 102b from the user 101.

At block 704, the station 100 accepts a used bottle from the user in response to the intake request. For example, the station 100 receives the bottle 102b via the bottle ingress 120. When the bottle 102b is received at the station 100, the station 100 begins an intake process for the used bottle at block 706. For example, the bottle handler 190 provides the used bottle from the bottle ingress 120 to the bottle inspection system 140.

At block 708, the station 100 performs a structural review of the used bottle. For example, as described in relation to FIG. 3, the bottle inspection system 140 examines the bottle 102c to verify that the bottle is compatible with the station 100. For example, the bottle inspection system 140 verifies the physical dimensions 326 and 325 and/or other bottle features such as the label 320 indicate the bottle 102c is compatible with the station 100. The bottle inspection system 140 also examines the bottle 102c to verify there is no damage to the bottle such as dents or cracks which may affect the function of the bottle. In some examples, when the bottle is incompatible with the station 100, the bottle is returned to the user 101 with an indication that the bottle is incompatible. In another example, the when the bottle is damaged as determined by the bottle inspection system 140, the user 101 is charged a bottle damage fee to cover any damage to the bottle.

At block 710, the station 100 determines whether to sanitize the used bottle and sanitizes the used bottle at block 712. For example, the station 100 determines that the bottle may be stored for external sanitation in bottle storage 170. In this example, the intake process proceeds to block 714. In an example, where the user bottle is to be stored in the bottle storage 160, the bottle handler 190 provides the bottle to the bottle sanitizer 150 where the bottle washer 405 provides a cleaning flow 406 to the bottle, such as the bottle 102d.

At block 714, the station 100 completes a charge for the bottle rental. For example, the station 100 reduces a bottle count associated with the user profile or user account when the user has an ongoing subscription with the station 100. In another example, where the user is pay-per-bottle, the station 100 completes or finalizes a charge for the user of the returned bottle.

At block 716, the station 100 determines whether the used bottle is sanitized. In an example, where the bottle is sanitized, the method 700 proceeds to block 718 where the station 100 stores the sanitized used bottle in a bottle storage structure such as the bottle storage 160. In an example, where the bottle is not sanitized the method 700 proceeds to block 720 where the station 100 stores the used bottle in a used bottle storage for external sanitation, such as the bottle storage 170.

At block 722, the station 100 updates the user account for the user with an indication of a returned bottle. In some examples, the station 100 also indicates to the user 101 via the display 106 that the bottle return is complete and the returned bottle is no longer associated with the user 101.

Figure 8:
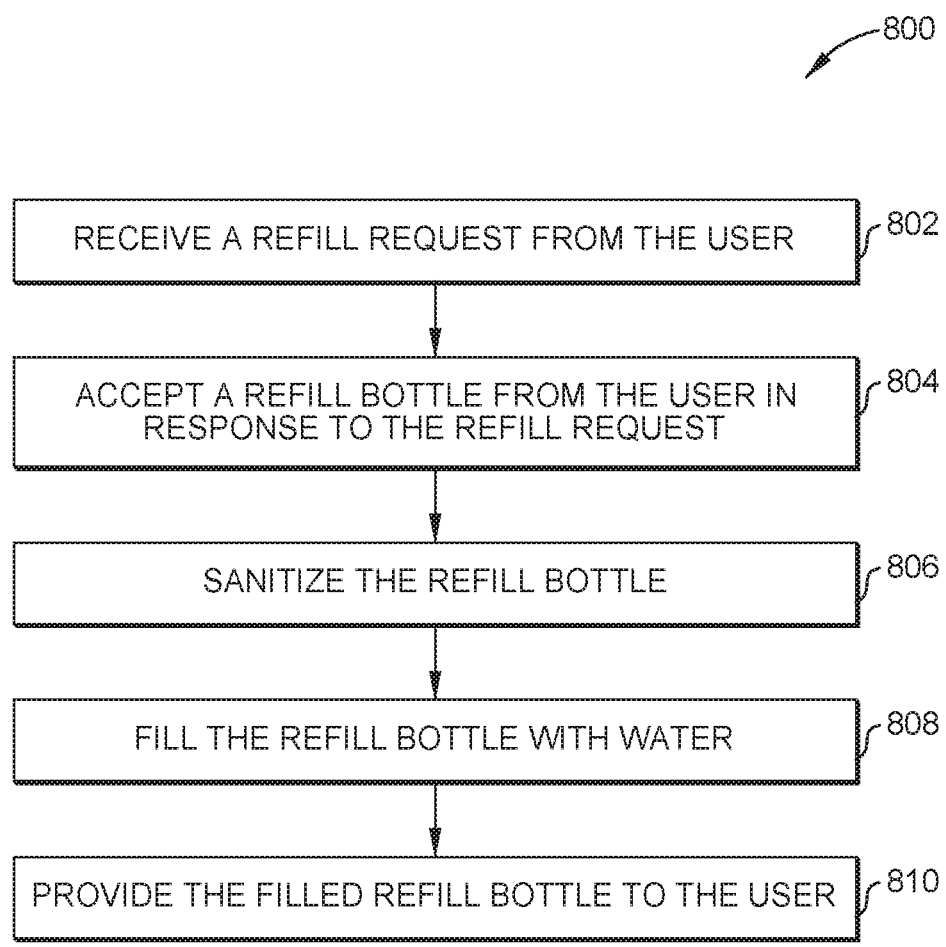
FIG. 8 is a method for refilling a bottle from a user, according to embodiments described herein.

FIG. 8 is a method 800 for refilling a bottle from a user, according to embodiments described herein. Method 800 begins at block 802 where the station 100 receives a refill request from the user. For example, the user may selected the UIE 210 to refill a bottle on the display 106 described in FIG. 2. In another example, the UIE 210 may be provided on the mobile device 103 such that the user does not need to physically interact with the display 106 on the station 100. The station 100 begins the process to provide the user 101 with a refilled bottle in response to the bottle request from the user 101.

At block 804, the station 100 accepts a refill bottle from the user in response to the refill request. For example, the station 100 receives the bottle 102b via the bottle ingress 120. In some examples, the bottle 102b may be visually examined by the system 140 to verify that the station 100 may process (e.g., sanitize and refill) the bottle. When the bottle 102b is received at the station 100, the station 100 begins a refill process for the used bottle at block 806. For example, the bottle handler 190 provides the used bottle from the bottle ingress 120 to the bottle sanitizer 150.

At block 806, the station 100 sanitizes the refill bottle. For example, the bottle washer 405 provides a cleaning flow 406 to the bottle, such as the bottle 102d in order to remove any debris from the bottle and sanitize the bottle. At block 808, the station 100 fills the refill bottle with liquid and provides the filled refill bottle to the user 101 at block 810. In some examples, the station 100 may also determine whether an enhancement selection has been received from the user 101 for the refill liquid. For example, the station 100 may receive a liquid enhancement selection from the user via the user interface 105. When an additive is selected, the station 100 provides a liquid additive with the liquid while filling the refill bottle.

In some examples, the station provides the refilled bottle to the user 101 via the bottle egress 110. In some examples, the user interface 105 is updated to indicate that the refilled bottle is ready for pick up by the user 101.

Figure 9:
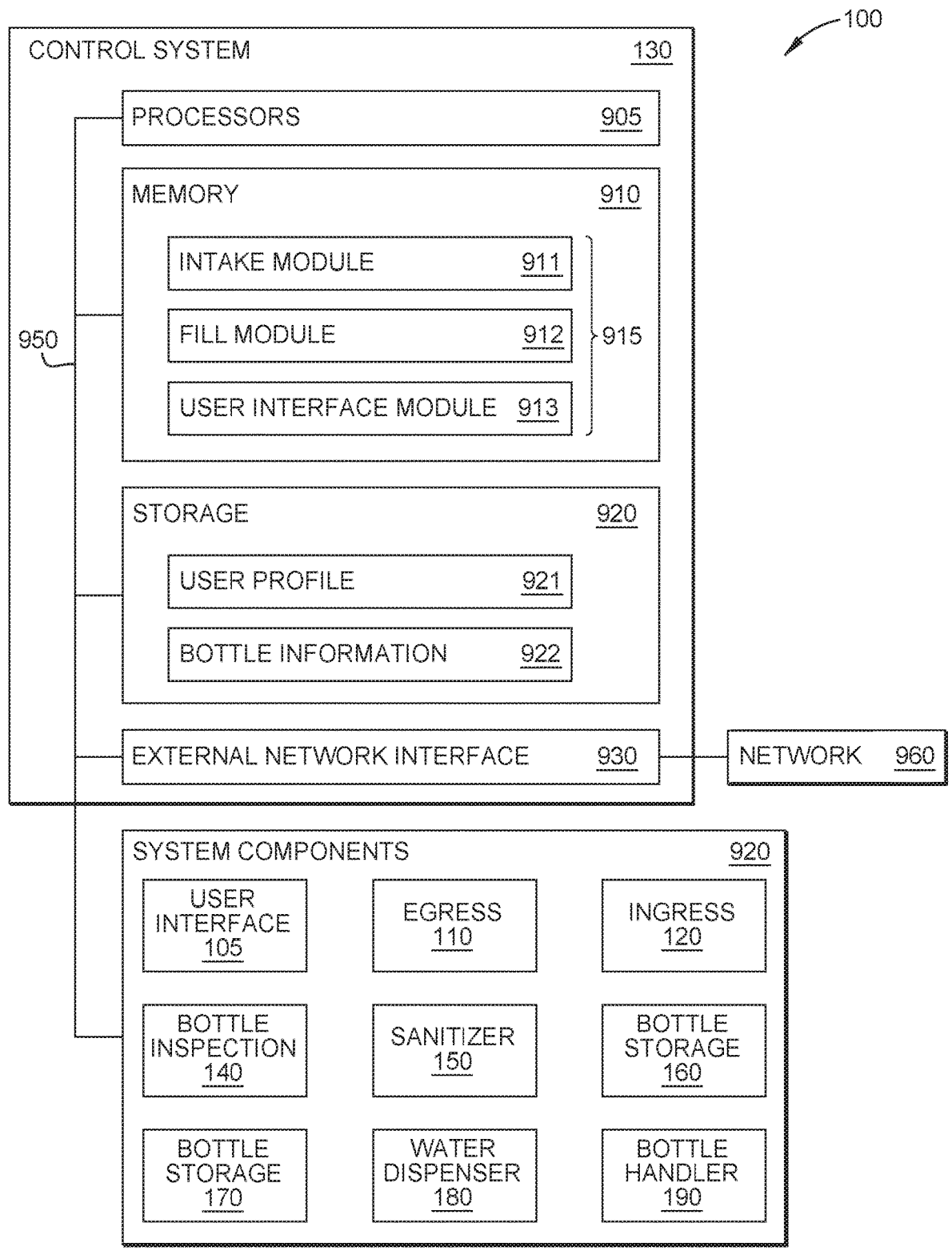
FIG. 9 is a block diagram of a control system for a bottle processing station according to embodiments described herein.

FIG. 9 is a block diagram of the control system 130 for a bottle processing station according to embodiments described herein. The control system 130 is shown in the form of a general-purpose computing device. The components of the control system 130 may include, but are not limited to, one or more processing units or processors 905, a memory 910, a storage system 920, network interface 930, and a bus 950 that couples various system components including the memory 910 and storage system 920 to processors 905 along with various input/output (I/O) and system components 940. In some embodiments, the station 100 is distributed and includes a plurality of discrete computing devices that are connected through wired or wireless networking, where the discrete computing devices control the various subsystems of the station 100 as shown in FIG. 1A.

Bus 950 and communication bus 115 described in FIG. 1A represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. The Bus 950 on the control system 130 may be connected to the communication bus 115.

Control system 130 typically includes a variety of computer system readable media. Such media may be any available media that is accessible by the control system 130, and it includes both volatile and non-volatile media, removable and non-removable media. Memory 910 can include computer system readable media in the form of volatile memory, such as random access memory (RAM) and/or cache memory. The control system 130 may further include other removable/non-removable, volatile/non-volatile computer system storage media. By way of example, storage system 920 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 950 by one or more data media interfaces. As will be further depicted and described below, memory 910 may include at least one program product having a set (e.g., at least one) of program modules that are configured to carry out the functions of embodiments of this disclosure.

The control system 130 may further include other removable/non-removable, volatile/non-volatile computer system storage media. In some examples, storage system 920 may be included as part of memory 910 and may typically provide a non-volatile memory for the networked computing devices, and may include one or more different storage elements such as Flash memory, a hard disk drive, a solid state drive, an optical storage device, and/or a magnetic storage device. For example, storage system 920 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 950 by one or more data media interfaces. Storage system 920 may include media for storing user profile 921 and bottle information 922. The storage system 920 may be updated and accessed by program modules 915 described herein.

Memory 910 may include a plurality of program modules 915 for performing various functions described herein. The program modules 915 generally include program code that is executable by one or more of the processors 905. As shown, program modules 915 include intake module 911, fill module 912, and user interface module 913.

The control system 130 may also communicate with system components 940 which include the various subsystems of the station 100 including the user interface 105, bottle egress 110, bottle ingress 120, bottle inspection system 140, bottle sanitizer 150, bottle storage 160, bottle storage 170, liquid dispenser 180, and bottle handler 190. Additionally, the control system 130 may communicate with one or more networks such as a network 960 which may include a local area network (LAN), a general wide area network (WAN), and/or a public network (e.g., the Internet) via network interface 930. As depicted, network interface 930 communicates with the other components of the control system 130 via bus 950. It should be understood that although not shown, other hardware and/or software components could be used in conjunction with control system 130. Examples, include, but are not limited to: cloud computing systems, microcode, device drivers, redundant processing units, external disk drive arrays, RAID systems, tape drives, and data archival storage systems, etc.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

While the foregoing is directed to embodiments of the present invention, other and further embodiments of the invention may be devised without departing from the basic scope thereof, and the scope thereof is determined by the claims that follow.

What is claimed is:

1. A method comprising:
    receiving a bottle request and a bottle intake request from a user;
    accepting a used bottle from the user in response to the bottle intake request;
    performing a structural review of the used bottle, via visual inspection sensors, to detect bottle damage to the used bottle and measure physical dimensions of the used bottle;
    when the used bottle is incompatible with a bottle system, based on the measured physical dimensions, returning the used bottle to the user with an indication of incompatibility;
    selecting a sanitized bottle from a sanitized bottle storage in response to the bottle request;
    associating the selected sanitized bottle to a user account for the user;
    charging the user account for a bottle rental;
    filling the associated bottle with liquid; and
    providing the filled bottle to the user.

2. The method of claim 1, further comprising:
    performing an intake process for the used bottle; and
    updating the user account for the user with an indication of a returned bottle.

3. The method of claim 2, wherein performing the intake process comprises:
    performing the structural review of the used bottle;
    sanitizing the used bottle;
    completing a charge for the bottle rental; and storing the sanitized used bottle in a bottle storage structure.

4. The method of claim 2, wherein performing the intake process comprises:
performing the structural review of the used bottle;
completing a charge for the bottle rental; and
storing the used bottle in a used bottle storage for external sanitation.

5. The method of claim 1, wherein the user account is associated with a bottle subscription service wherein the associating the selected bottle to the user account comprises:
verifying the user is a member of the bottle subscription service;
wherein when the user is not a member of the bottle subscription service:
intaking the user as a new member of the bottle subscription service; and
wherein when the user is a member of the bottle subscription service:
verifying a payment method or paid subscription for the user; and
updating a bottle count associated with the user with the selected bottle.

6. The method of claim 1, wherein filling the associated bottle with liquid comprises:
receiving an enhancement selection from the user; and
providing an additive with the liquid while filling the selected bottle.

7. The method of claim 1, wherein the user account is associated with a health profile for the user, wherein the method further comprises:
determining an amount of liquid in the filled bottle; and
updating a liquid tracking count for the user in the health profile for the user.

8. The method of claim 1, further comprising:
receiving a refill request from the user;
accepting a refill bottle from the user in response to the refill request;
sanitizing the refill bottle;
filling the refill bottle with liquid; and
providing the filled refill bottle to the user.

9. A system for bottle rental and sharing comprising:
a sanitized bottle storage structure comprising at least one bottle;
visual inspection sensors;
a bottle sanitizer;
a user interaction system comprising a user interface and a bottle egress;
a liquid dispenser; and
a control system comprising one or more computer processors and a memory containing a program which when executed by the computer processors performs an operation comprising:
receiving a bottle request and a bottle intake request from a user via the user interaction system;
accepting a used bottle from the user in response to the bottle intake request;
performing a structural review of the used bottle, via the visual inspection sensors, to detect bottle damage to the used bottle and measure physical dimensions of the used bottle;
when the used bottle is incompatible with the bottle system, based on the measured physical dimensions, returning the used bottle to the user with an indication of incompatibility;
selecting a sanitized bottle from the sanitized bottle storage structure;
associating the selected sanitized bottle to a user account for the user;
charging the user account for a bottle rental;
filling the associated bottle with liquid via the liquid dispenser; and
providing the filled bottle to the user via the bottle egress.

10. The system of claim 9, wherein the user interaction system further comprises a bottle ingress;
wherein the operation further comprises:
receiving the bottle intake request from the user via the user interface;
performing an intake process for the used bottle; and
updating the user account for the user with an indication of a returned bottle.

11. The system of claim 10, wherein the system further comprises:
a bottle inspection system; and
a bottle sanitizer; and
wherein performing the intake process comprises:
performing the structural review of the used bottle via the bottle inspection system;
sanitizing the used bottle via the bottle sanitizer;
completing a charge for the bottle rental; and
storing the sanitized used bottle in the bottle storage structure.

12. The system of claim 10, wherein the system further comprises:
a bottle inspection system; and
a bottle sanitizer; and
wherein performing the intake process comprises:
performing the structural review of the used bottle via the bottle inspection system;
completing a charge for the bottle rental; and
storing the used bottle in a used bottle storage for external sanitation.

13. The system of claim 9, wherein the user account is associated with a bottle subscription service wherein the associating the selected bottle to the user account comprises:
verifying the user is a member of the bottle subscription service;
wherein when the user is not a member of the bottle subscription service:
intaking the user as a new member of the bottle subscription service; and
wherein when the user is a member of the bottle subscription service:
verifying a payment method or paid subscription for the user; and
updating a bottle count associated with the user with the selected bottle.

14. The system of claim 9, wherein filling the associated bottle with liquid comprises:
receiving a liquid enhancement selection from the user via the user interface; and
providing a liquid additive with the liquid while filling the selected bottle at the liquid dispenser.

15. The system of claim 9, wherein the user account is associated with a health profile for the user, wherein the operation further comprises:
determining an amount of liquid in the filled bottle; and
updating a liquid tracking count for the user in the health profile for the user.

16. The system of claim 9, wherein the system further comprises:
a bottle sanitizer;
a bottle ingress; and wherein the operation further comprises:
receiving a refill request from the user via the user interface;
accepting a refill bottle from the user in response to the refill request via the bottle ingress;
sanitizing the refill bottle via the bottle sanitizer;
filling the refill bottle with liquid via the liquid dispenser; and
providing the filled refill bottle to the user via the bottle egress.

17. A computer program product for bottle rental and sharing, the computer program product comprising:
a computer-readable storage medium having computer-readable program code embodied therewith, the computer-readable program code executable by one or more computer processors to perform an operation comprising:
receiving a bottle request and a bottle intake request from a user;
accepting a used bottle from the user in response to the bottle intake request;
performing a structural review of the used bottle, via visual inspection sensors, to detect bottle damage to the used bottle and measure physical dimensions of the used bottle;
when the used bottle is incompatible with a bottle system, based on the measured physical dimensions, returning the used bottle to the user with an indication of incompatibility;
selecting a sanitized bottle from a sanitized bottle storage in response to the bottle request;
associating the selected sanitized bottle to a user account for the user;
charging the user account for a bottle rental;
filling the associated bottle with liquid; and
providing the filled bottle to the user.

18. The computer program product of claim 17, wherein the operation further comprises:
performing an intake process for the used bottle; and
updating the user account for the user with an indication of a returned bottle.

19. The computer program product of claim 18, wherein performing the intake process comprises:
performing the structural review of the used bottle;
sanitizing the used bottle;
completing a charge for the bottle rental; and
storing the sanitized used bottle in a bottle storage structure.

20. The computer program product of claim 17, wherein the operation further comprises:
receiving a refill request from the user;
accepting a refill bottle from the user in response to the refill request;
sanitizing the refill bottle;
filling the refill bottle with liquid; and
providing the filled refill bottle to the user.

\* \* \* \* \*